United States Patent [19]

Neckers

[11] Patent Number: 4,849,076
[45] Date of Patent: Jul. 18, 1989

[54] CONTINUOUS OXIDATION METHOD

[76] Inventor: Douglas C. Neckers, 108 Secor Woods La., Perrysburg, Ohio 43551

[21] Appl. No.: 107,682

[22] Filed: Oct. 13, 1987

[51] Int. Cl.[4] ......................... B01J 19/08; C08F 8/00; C08G 69/48
[52] U.S. Cl. ............................. 204/157.15; 204/157.6; 204/157.69; 204/157.93; 204/157.92; 204/157.87; 204/157.88; 204/158.14; 204/193; 422/186
[58] Field of Search ...................... 204/157.15, 157.41, 204/157.61, 157.6, 157.69, 157.87, 157.88, 157.89, 157.9, 157.92, 157.93, 157.94, 158.14, 193; 422/186, 186.3

[56] References Cited

U.S. PATENT DOCUMENTS 3,169,103  2/1965  Falcone ............................ 204/157.6
4,315,998  2/1982  Neckers et al. ..................... 525/332

Primary Examiner—John F. Niebling
Assistant Examiner—Ben C. Hsing
Attorney, Agent, or Firm—John C. Purdue; David C. Purdue

[57] ABSTRACT

A method for oxidizing a substrate which is oxidizable by singlet oxygen is discolded. The first step of the method comprises establishing a flow to and from each of a plurality of successive closed zones, each of which zones
(a) contains a quantity of a polymer-bound photosensitizing catalyst that is a source for singlet oxygen when irradiated by light of a particular wavelength, and
(b) is of such size and shape that a major portion of the catalyst therein can be made a source for singlet oxygen by irradiation with light of a suitable wavelength.

The flow is established by charging the substrate in the liquid phase into the first zone, removing reaction product from the last zone, and transferring reaction product from the first zone and from each intermediate zone to the next succeeding zone. Oxygen is introduced into each of the zones and each is irradiated with light of a frequency which causes the catalyst to be a source for singlet oxygen.

1 Claim, 2 Drawing Sheets

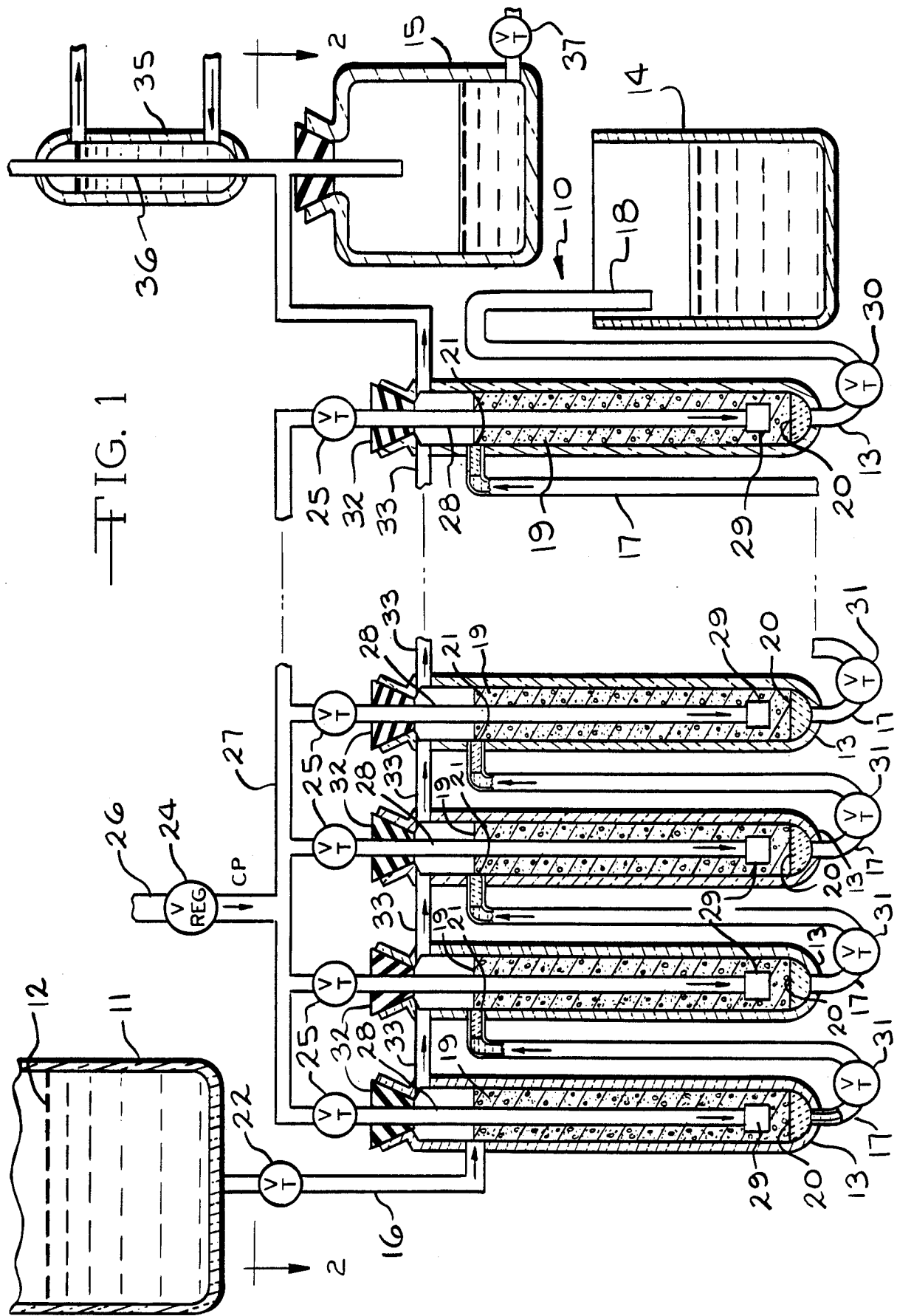

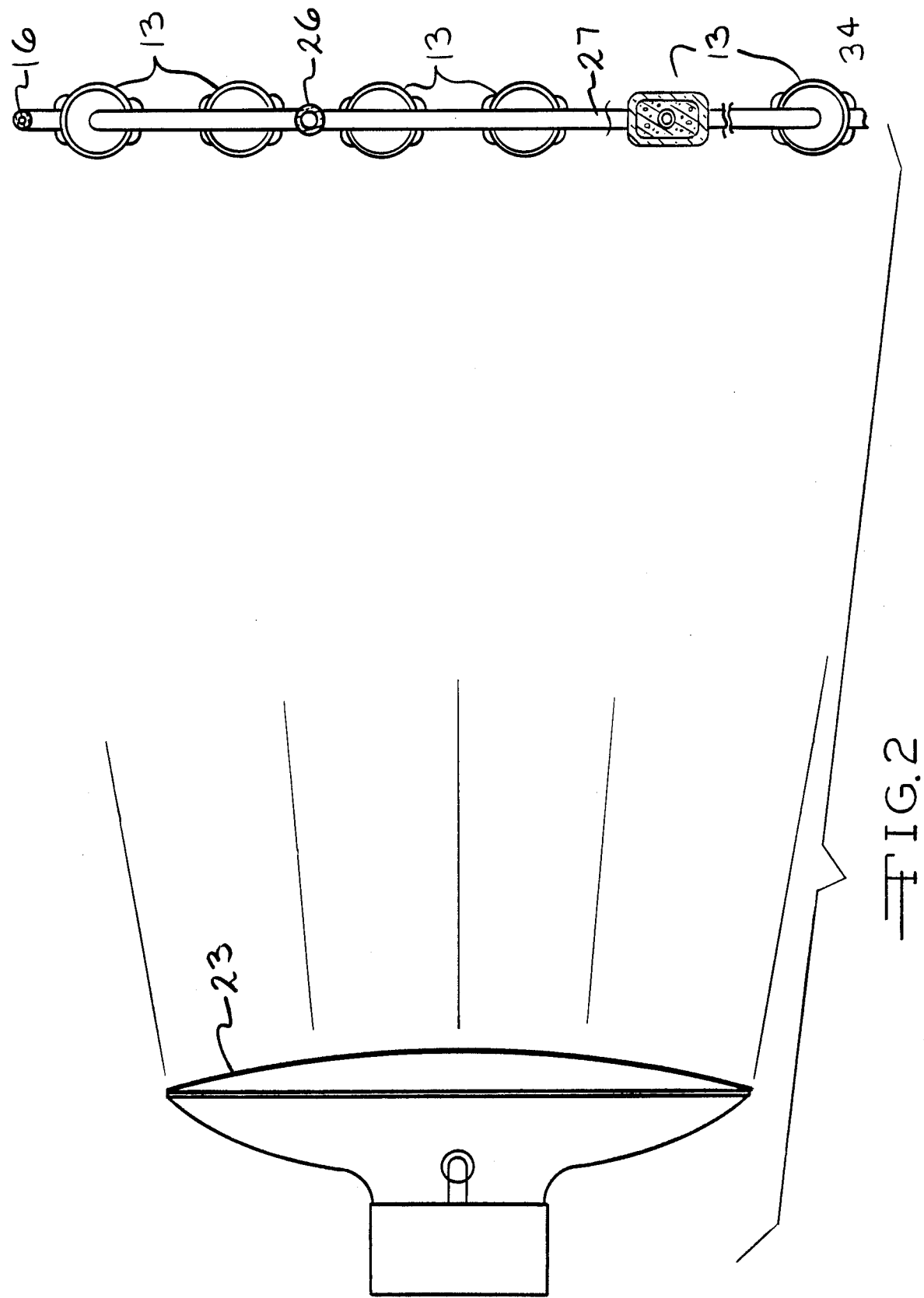

CONTINUOUS OXIDATION METHOD

DEFINITIONS

As used herein, and in the appended claims, the terms "percent" and "parts" refer to percent and parts by weight, unless otherwise indicated; g means gram or grams; cm means centimeter or centimeters; mm means millimeter or millimeters; m/o means mole percent; v/o means volume percent; psi means pounds per square inch; and MPa means $10^6$ Pascals.

All temperatures herein are in degrees C., unless otherwise indicated.

BACKGROUND OF THE INVENTION

1. Field of the Invention

The instant invention is a continuous method for oxidizing a substrate which is oxidizable by singlet oxygen. The method involves the steps of establishing a flow to and from each of a plurality of successive closed zones by charging the substrate in the liquid phase to the first zone, removing reaction product from the last zone, and transferring reaction product from the first zone and from each intermediate zone to the next succeeding zone. Each zone contains a quantity of a polymer-bound photosensitizing catalyst that is a source for singlet oxygen when irradiated by light of a particular wavelength, and is of such size and shape that a major portion of the catalyst therein can be made a source for singlet oxygen by irradiation with light of a suitable wavelength. Oxygen is introduced into each of the zones, and each is irradiated with light of a wavelength which causes the catalyst to be a source for singlet oxygen.

2. The Prior Art

Polymer-bound photosensitizing catalysts that are a source for singlet oxygen when irradiated by light of a particular wavelength are known, being disclosed, for example, by U.S. Pat. No. 4,315,998 granted to Neckers et al. on Feb. 16, 1982. The patent discloses, by way of illustration, the production of a polymer-bound photosensitizing catalysts from cross-linked polystyrene and chloromethylatedstyrene-divinylbenzene copolymer beads by reaction with acridine orange, chlorophyllin, crystal violet, Eosin Y, fluorescein, flavin mononucleotide, hematoporphyrin, hemin, malachite green, methylene blue, rhodamine B and rose bengal. The patent also discloses the production of polymer-bound photosensitizing catalysts where the polymer is a poly(2-hydroxyethyl)methacrylate 5 percent ethylene glycol polymer, a poly(2-hydroxyethyl)methacrylate 60 percent ethylene glycol polymer, a polyvinyl formal, a bromomethylated borosilicate glass, a styrenemaleic anhydride copolymer, and a polymer produced by reaction between sebacoyl chloride and hexamethylene diamine.

The Neckers et al. patent also discloses the use of the polymer-bound photosensitizing catalysts, for example, for the oxidation of 1,2-diphenyl-p-dioxene, 1,3-cyclohexadiene, tetramethylethylene, 1,2-dimethylcyclohexene and dihydropyran. The patent describes in detail only two procedures which involve the photooxidation of a substrate using a polymer-bound photosensitizing catalyst. One of these procedures, described in Example 22, involved the photooxidation of 140 milligrams of 1,2-diphenyl-p-dioxene and a six hour reaction, while the other, described in Example 31, involved the photooxidation of 97 milligrams of 2,3-diphenyl-p-dioxene and a 2–4 hour reaction time. Other photooxidation procedures described in the patent incorporate by reference the technique of Example 22. It will be appreciated that the photooxidation procedures described in the Neckers et al. patent are time-consuming batch processes where minute quantities of a substrate and of a polymer bound catalyst are charged to a single vessel and irradiated in the presence of oxygen to produce minute quantities of the oxidation products, and that the syntheses cannot be scaled up by charging larger quantities of the oxidizable substrates because light, which is necessary to cause the catalyst to be a source for singlet oxygen, is able to penetrate only a comparatively short distance into the reaction mixture.

BRIEF DESCRIPTION OF THE INSTANT INVENTION

The instant invention is based upon the discovery of a method for oxidizing a substrate which is oxidizable by singlet oxygen, which method includes the step of establishing a flow to and from each of a plurality of successive closed zones by charging the substrate in the liquid phase to the first zone, removing reaction product from the last zone, and transferring reaction product from the first zone and from each intermediate zone to the next succeeding zone. Each of the zones contains a quantity of a polymer-bound photosensitizing catalyst that is a source for singlet oxygen when irradiated by light of a particular wavelength, and is of such size and shape that a major portion of the catalyst therein can be made a source for singlet oxygen by irradiation with light of a suitable wavelength. Oxygen is introduced into each of the zones, and each is irradiated with light of a wavelength which causes the catalyst to be a source for singlet oxygen. It has been found that the rate of reaction varies as a direct function of the amount of polymer-bound catalyst in each of the closed zones, other factors being equal, as that amount varies from a small amount to a somewhat larger amount, and then remains substantially constant with further increases in amount. It has also been found that the rate of reaction varies as a direct function of the intensity of the light used to irradiate the catalyst in each of the closed zones, other factors being equal, as that intensity varies from a low intensity to one somewhat higher, and then remains substantially constant with further increases in intensity. As a consequence, in practicing the instant invention, it is possible to use substantially the minimum amount of catalyst in each of the closed zones that enables the maximum rate of reaction, and to use substantially the minimum light intensity that enables the maximum rate of reaction, thereby minimizing the amount of polymer-bound catalyst required, and also minimizing the light intensity that is required.

It is, therefore, an object of the instant invention to provide a continuous method for oxidizing a substrate which is oxidizable by singlet oxygen, using a polymer-bound photosensitizing catalyst that is a source for singlet oxygen when irradiated by light of a particular wavelength.

Other objects and advantages of the invention will be apparent from the description which follows of preferred embodiments thereof.

BRIEF DESCRIPTION OF THE DRAWINGS

FIG. 1 of the attached drawings is a view in vertical section showing the continuous oxidation of a substrate according to the invention and apparatus for carrying out that oxidation.

FIG. 2 is a plan view of the apparatus of FIG. 1.

DESCRIPTION OF THE PREFERRED EMBODIMENTS

Referring to FIG. 1, apparatus indicated generally at 10 can be used to practice the instant invention. The apparatus 10 includes a vessel 11 which contains a quantity of a substrate 12 to be oxidized, a plurality of reaction vessels 13, a receiver 14 for the reaction product, and a receiver 15 for solvent. A tube 16 connects the first of the reaction vessels 13 to the vessel 11, while a tube 17 connects the first of the reaction vessels to the second, the second to the third *** and the penultimate to the last, and a tube 18 connects the last of the reaction vessels 13 to the receiver 14. Each of the reaction vessels 13 is packed with a polymer-bound photosensitizing catalyst, designated 19. A porous ceramic member 20 at the bottom of each of the reaction vessels 13 prevents the catalyst 19 from flowing from the bottoms of the reaction vessels 13 into the tubes 17, while a porous ceramic member 21 at the top of each of the tubes 17 prevents the catalyst 19 from flowing from the tops of the reaction vessels 13 into the tubes 17.

When the apparatus 10 is in operation practicing the instant invention: a valve 22 is open as required to enable the substrate 12 to flow at a desired rate into the first of the reaction vessels 13; light sources 23 (one of which is shown in FIG. 2) on both sides of the vessels 13 are energized; valves 24 and 25 (FIG. 1) are open as required to enable oxygen to flow at a desired rate from a supply (not illustrated) through a tube 26 into a manifold 27 and from thence through tubes 28 and diffusers 29 into the bottom of each of the reaction vessels 13; a valve 30 is open as required to enable product to flow through the tube 19 into the receiver 14; and valves 31 are open as required to enable reaction product to flow from the first and from each intermediate one of the reaction vessels 13 through one of the tubes 17 to the next of the reaction vessels 13.

Each of the tubes 28 extends through a resilient stopper 32 in the mouth thereof into the interior of one of the reaction vessels 13. In practice, as shown, the level of reaction product in each of the vessels 13 is maintained below the stopper 32, so that excess oxygen or, if air rather than pure oxygen is used in practicing the method, a mixture of excess oxygen and nitrogen can collect below the stopper and above the liquid level in each of the vessels 13. The oxygen, oxygen and nitrogen, or the like can flow through tubes 33 from the first and each intermediate vessel 13 to the last vessel 13, and from there through a gas discharge tube 34 which is vented through a reflux condenser 35. Cold water is circulated through the reflux condenser 35 to condense any solvent that may have been vaporized in the apparatus 10. Gases are vented from a central tube 36 of the reflux condenser 35, while condensed solvent flows downwardly into the receiver 15.

The relationship between one of the light sources 23 and the reaction vessels 13 is shown in FIG. 2, that light source being shown as illuminating one side of each of the reaction vessels 13. The second light source 23 (not illustrated in FIG 2) is similarly positioned, but to illuminate the opposite side of each of the reaction vessels 13. The reaction proceeds only in the presence of singlet oxygen, which forms only when the polymer-bound catalyst is irradiated by light of a suitable wavelength in the presence of oxygen. It has been found that light is capable of causing the formation of singlet oxygen at only a comparatively short distance, usually not more than about 5 mm, into a substrate to be oxidized or into a solution of such a substrate. Accordingly, for maximum reaction rates, the vessels 13 should be comparatively thin in the direction in which irradiating light travels therethrough. For example, if only one irradiating light is used, maximum reaction rates are achieved if the vessels are not thicker than about 5 mm in this dimension while, if two lights are used, one on each side of the vessels 13, maximum reaction rates can be achieved at thicknesses in this dimension up to about 10 mm. Similarly, while substantial reaction rates can be achieved with two lights, one on each side of the vessels 13, or even with one light, the vessels 13 can also be arranged in a circle and surrounded with lights of a suitable wave length. The over-all reaction rate can be increased by increasing the rate at which the substrate is charged, thus decreasing the residence time in each of the vessels 13, and using a correspondingly larger number of vessels to achieve the desired extent of oxidation. In this case, it will often be desirable to use two or more lights, or two or more lights on each side of the vessels, or to arrange the vessels in a circle and surround them with lights to provide substantially the same light intensity to each.

It will be appreciated that the method of the invention is preferably practiced over an extended period of time because the concentration of the reaction product, when the method is being practiced, increases progressively from the first to the last of the vessels 13 and the concentration of the substrate being oxidized decreases correspondingly. This concentration gradient can be approximated, on start up, by mixing the final product, in varying proportions, with the substrate to be oxidized or a solution thereof in a suitable solvent and charging different concentrations of the final product to the different vessels 13. It can also be approximated by charging all of the vessels 13 with the substrate to be oxidized, or with a solution of the substrate in a suitable solvent, irradiating each of the vessels 13 with light of a suitable wavelength, and bubbling air or oxygen through the different vessels 13 for varying periods of time, the longest for the last of the vessels 13 and the shortest for the first. In either case, operation can then proceed as described above.

Apparatus similar to that shown in the attached drawings and described in connection therewith has been used, as described in the following Examples, to carry out oxidations of several substrates by singlet oxygen formed by irradiating polymer-bound photosensitizing catalysts with light of a suitable wavelength in the presence of oxygen. In all cases, the reaction was carried out using polymer bound rose bengal produced as described in Example 1 of Neckers et al. U.S. Pat. No. 4,315,998 as the catalyst, and produced the known products of the singlet oxygen oxidation of the substrates. For example, such oxidation of 1,2-diphenyl-p-dioxane produced ethylene glycol dibenzoate, while such oxidation of tetramethyl ethylene produced an allylic hydroperoxide, such oxidation of 3,4-dihydropyran produced a mixture of an aldehyde and a hydroperoxide, and such oxidation of 1,3-cyclohexadiene produced a cyclic peroxide. The formulas for the products of the oxidations of the last three substrates are given in U.S. Pat. No. 4,315,998. Other substrates whose oxidations with singlet oxygen are known include $11\beta,21$- dihydroxy-1,4,17(20)cis-preg-natrien-3-one, α-Terpenene and α-Pinene. The Examples which follow are presented solely for the purpose of further illustrating and disclosing the invention and are not to be construed as limiting.

EXAMPLE 1

Reaction vessels 13, each of which had a capacity of 100 ml, were charged with 5 g polymer rose bengal and 5 g dichloromethane, and a solution in dichloromethane containing 0.084 g per ml tetramethylethylene was introduced into the vessel 11 of the apparatus of FIG. 1. The apparatus was then placed in a cold room where a temperature of 7° was maintained. After the apparatus reached temperature equilibrium, the valve 22 was controlled to cause the tetramethylethylene solution to flow at a rate of 100 ml per hour from the vessel 11 into the first of seven reaction vessels 13. The light sources 23, which emitted broad band radiation centered at 500 μm, were positioned so that the light intensity approximated $10^{15}$ to $10^{17}$ quanta per minute on the exteriors of the reaction vessels 13. Air was bubbled into each of the vessels 13 at a rate sufficient to maintain the solution in each saturated with air. The percentage of tetramethylethylene in the solute in each of the reaction vessels was determined periodically, and was found to reach a steady state in the first five vessels after about 3 hours. The percentage were as follows: in the first vessel, 83 percent of the solute was tetramethylethylene; in the second, 63 percent; in the third, 50 percent; in the fourth 32 percent; and in the fifth, 20 percent. In the sixth and seventh vessels, a steady state was reached after about 4 hours, at 8 percent tetramethylethylene in the former and at 2 percent in the latter.

The procedure described above was repeated, except that the tetramethylethylene solution was introduced into the first of the reaction vessels at a rate of 50 ml per hour. A steady state was reached in the first vessel after about 3 hours with 82 percent of the solute tetramethylethylene, in the second vessel after about 6 hours with 54 percent of the solute tetramethylethylene, after about six hours in the third vessel with 27 percent of the solute tetramethylethylene, and after about seven hours in the fourth vessel with six percent of the solute tetramethylethylene.

EXAMPLE 2

The procedure of Example 1 was repeated, except that a solution of 0.02 g per ml 1,2-diphenyl-p-dioxene was introduced into the vessel 11. A steady state was achieved in all seven vessels after about 2 hours. The percent of the solute in each of the vessels which was 1,2-diphenyl-p-dioxene was as follows:

| Vessel No. | Percent 1,2-diphenyl-p-dioxene |
| --- | --- |
| 1 | 84 |
| 2 | 62 |
| 3 | 48 |
| 4 | 35 |
| 5 | 20 |
| 6 | 9 |
| 7 | 3 |

When a concentration of 0.006 g per ml 1,2-diphenyl-p-dioxene was used, the percent thereof in each of the vessels was as follows:

| Vessel No. | Percent 1,2-diphenyl-p-dioxene |
| --- | --- |
| 1 | 62 |
| 2 | 35 |
| 3 | 17 |
| 4 | 5 |
| 5 | 1 |
| 6 | 0 |
| 7 | 0 |

EXAMPLE 3

The procedure of Example 1 was repeated, except that a solution of 0.02 g per ml 3,4-dihydropyran was introduced into the vessel 11. At steady state, the percent of the solute in each of the vessels which was 3,4-dihydropyran was as follows:

| Vessel No. | Percent 3,4-dihydropyran |
| --- | --- |
| 1 | 99 |
| 2 | 98 |
| 3 | 97 |
| 4 | 96 |
| 5 | 95 |
| 6 | 94 |
| 7 | 93 |

The foregoing data indicate that a large number of stages would be required for the complete oxidation of dihydropyran under the conditions employed. A similar result was achieved when a solution of 0.0156 g per ml 11β,21-dihydroxy-1,4,17(20)cis-preg-natrien-3-one in a solvent composed of 90 v/o dichloromethane and 10 v/o methanol was introduced into the vessel 11.

EXAMPLE 4

The procedure of Example 1 was repeated, except that a solution of 0.021 g per ml 1,3-cyclohexadiene was introduced into the vessel 11. After a steady state was achieved the percent of the solute in each of the vessels which was 1,3-cyclohexadiene was as follows:

| Vessel No. | Percent 1,3-cyclohexadiene |
| --- | --- |
| 1 | 88 |
| 2 | 75 |
| 3 | 63 |
| 4 | 52 |
| 5 | 40 |
| 6 | 28 |
| 7 | 19 |

When a concentration of 0.018 g per ml 1,3-cyclohexadiene was used, the percent thereof in each of the vessels was as follows:

| Vessel No. | Percent 1,3-cyclohexadiene |
| --- | --- |
| 1 | 81 |
| 2 | 73 |
| 3 | 63 |
| 4 | 54 |
| 5 | 39 |
| 6 | 25 |
| 7 | 20 |

The procedure of Example 1 was repeated, except that a solution of 0.021 g per ml 1,3-cyclohexadiene was introduced into the vessels 11 and caused to flow at a rate of 25 ml per hour into the first of the vessels 13.

After a steady state was achieved the percent of the solute in each of the vessels which was 1,3-cyclohexadiene was as follows:

| Vessel No. | Percent 1,3-cyclohexadiene |
|---|---|
| 1 | 88 |
| 2 | 58 |
| 3 | 18 |
| 4 | 6 |

EXAMPLE 5

The procedure of Example 1 was repeated, except that a solution of 0.0125 g per ml α-terpenene was introduced into the vessel 11. After a steady state was achieved the percent of the solute in each of the vessels which was α-terpenene was as follows:

| Vessel No. | Percent α-terpenene |
|---|---|
| 1 | 50 |
| 2 | 9 |
| 3 | 7 |
| 4 | 7 |
| 5 | 7 |
| 6 | 7 |
| 7 | 7 |

EXAMPLE 6

The procedure of Example 1 was repeated, except that a solution of 0.01 g per ml α-pinene was introduced into the vessel 11. After a steady state was achieved the percent of the solute in each of the vessels which was α-pinene was as follows:

| Vessel No. | Percent α-pinene |
|---|---|
| 1 | 98 |
| 2 | 97 |
| 3 | 95 |
| 4 | 94 |
| 5 | 92 |
| 6 | 91 |
| 7 | 89 |

When a concentration of 0.002 g per ml α-pinene was used the percent thereof in each of the vessels was as follows:

| Vessel No. | Percent α-pinene |
|---|---|
| 1 | 97 |
| 2 | 94 |
| 3 | 91 |
| 4 | 88 |
| 5 | 85 |
| 6 | 82 |
| 7 | 79 |

It will be appreciated that various changes and modifications can be made from the details of the instant invention as described herein without departing from the spirit and scope thereof as defined in the appended claim. For example, each of the closed zones can be a coil containing the polymer rose bengal or other catalyst, and the substrate or substrate solution can flow continuously into the first coil while a reaction mixture flows from the first coil and from each subsequent coil into the next coil of the reactor system.

What I claim is:

1. In a method for oxidizing a substrate which is oxidizable by singlet oxygen, to produce a reaction product which method comprises the steps of
   (1) introducing a quantity of the substrate in the liquid phase into a closed zone
      (a) containing a quantity of a polymer-bound photosensitizing catalyst that is a source for singlet oxygen when irradiated by light of a particular wavelength in the presence of oxygen, and
      (b) of a size and shape that a major portion of the catalyst therein can be made a source for singlet oxygen by irradiation in the presence of oxygen with light of a suitable wavelength, and
   (2) introducing oxygen into the closed zone while irradiating the catalyst therein with light of a frequency which causes the catalyst to be a source for singlet oxygen, the improvement of carrying out the oxidation in a plurality of said closed zones, each of which contains the photosensitizing catalyst, said plurality including a first zone, a last zone, and at least one intermediate zone, by charging the substrate in the liquid phase into the first zone, removing reaction product from the last zone, and transferring reaction product from the first zone and from each intermediate zone to the next succeeding zone, while introducing oxygen into each of the zones and irradiating each with light of a frequency which causes the catalyst to be a source for singlet oxygen.

* * * * *